United States Patent
Overkempe

(10) Patent No.: US 12,077,486 B2
(45) Date of Patent: Sep. 3, 2024

(54) QUATERNARY FATTY AMIDOAMINE DETERGENTS

(71) Applicant: NOURYON CHEMICALS INTERNATIONAL B.V., Arnhem (NL)

(72) Inventor: Kornelis Overkempe, Holten (NL)

(73) Assignee: NOURYON CHEMICALS INTERNATIONAL B.V., Arnhem (NL)

( * ) Notice: Subject to any disclaimer, the term of this patent is extended or adjusted under 35 U.S.C. 154(b) by 555 days.

(21) Appl. No.: 17/298,063

(22) PCT Filed: Nov. 29, 2019

(86) PCT No.: PCT/EP2019/083193
§ 371 (c)(1),
(2) Date: May 28, 2021

(87) PCT Pub. No.: WO2020/109613
PCT Pub. Date: Jun. 4, 2020

(65) Prior Publication Data
US 2022/0177415 A1    Jun. 9, 2022

(30) Foreign Application Priority Data
Nov. 30, 2018  (EP) .................... 18209606

(51) Int. Cl.
*C07C 231/02* (2006.01)
*A01N 25/30* (2006.01)
*C07C 231/12* (2006.01)
*C11D 1/62* (2006.01)

(52) U.S. Cl.
CPC ............ *C07C 231/02* (2013.01); *A01N 25/30* (2013.01); *C07C 231/12* (2013.01); *C11D 1/62* (2013.01)

(58) Field of Classification Search
CPC ........ C07C 231/02; C07C 231/12; C11D 1/62
See application file for complete search history.

(56) References Cited

U.S. PATENT DOCUMENTS

| | | | |
|---|---|---|---|
| 3,401,119 A | 9/1968 | Froehlich | |
| 5,117,058 A | 5/1992 | Chen et al. | |
| 5,242,492 A | 9/1993 | Krivohlavek | |
| 5,254,271 A * | 10/1993 | Hamann | C11D 3/0015 424/70.28 |
| 5,344,642 A | 9/1994 | Hintz et al. | |
| 6,107,352 A * | 8/2000 | Zofchak | A61Q 19/10 516/914 |

FOREIGN PATENT DOCUMENTS

| | | |
|---|---|---|
| DE | 195 03 277 C1 | 5/1996 |
| EP | 0 507 003 A2 | 10/1992 |
| GB | 1 601 815 A | 11/1981 |
| WO | 99 54027 A1 | 10/1999 |

* cited by examiner

*Primary Examiner* — Yate' K Cutliff
(74) *Attorney, Agent, or Firm* — LORENZ & KOPF, LLP

(57) ABSTRACT

The invention relates to specific quaternary amidoamine detergents, the process to make them, and their use. The quaternary amidoamine detergents are obtainable by reacting a multifunctional acid with an amino amine, followed by quaternization, suitably with dimethyl carbonate, and subsequent reaction with a fatty acid. In the process to make the quaternary amidoamine detergents a multifunctional fatty acid is reacted with an amino amine, typically an amino alkylene amine, followed by quaternization with a quaternizing agent and subsequent replacement of the anion of said quaternizing agent with a fatty acid anion. The quaternary fatty amidoamine detergents are particularly useful as a surface-active compound that is soluble in an a-polar medium, for example when used as a stabilizer for solids in an a-polar medium.

19 Claims, No Drawings

QUATERNARY FATTY AMIDOAMINE DETERGENTS

This application is a 371 of PCT/EP2019/083193, filed Nov. 29, 2019, which claims foreign priority benefit under 35 U.S.C. § 119 of European Patent Application No. 18209606.5, filed Nov. 30, 2018, the disclosures of which are incorporated herein by reference.

FIELD OF THE INVENTION

Many detergents are known. By definition a detergent is an agent that cleans. The majority of detergents are surface-active agents, such as soaps. Their mode of action is the lowering of the surface and interfacial tension of solutions in which they are present and they are typically strongly adhering to surfaces and other phase boundaries. Therefore, they are used for various applications, including those to disperse solids in liquids. Examples of such a use are hard surface cleaning, including dishwashing, and the stabilization of suspensions, including suspension concentrates of agrochemicals and particles in cutting oils. The present invention relates to specific detergents that are oil-soluble, also known as being hydrophobic in nature.

BACKGROUND OF INVENTION

As said, the detergents are typically dissolved in a medium. For good solubility in a-polar media, such as oils, the detergents used therein are typically of a hydrophobic nature with relatively few ionic groups.

U.S. Pat. No. 3,401,119 discloses products of fatty acids and amines which are quaternized with diethyl sulfate and used in various applications.

GB1601815 discloses how a dimeric fatty acid is reacted with dimethyl amino propyl amine and subsequently quaternized. The product, however, is water-soluble, and used in the process of dying fibres.

DE19503277 to Henkel shows reaction of dimeric fatty acid with amines and quaternization thereof with DMS for use in hair care and textile, whereby the products are typically deposited on a substrate and not used as a detergent.

EP0507003 relates to fabric softener products with counterions that are water-soluble. The products are salts of acids and amines or quaternary ammonium compounds of dimethylsulfate, or both. The products do not provide the needed solubility in a-polar media and there is no disclosure wherein the anion of a quaternary material is exchanged.

WO 99/054027 relates to emollients and conditioners for use in cosmetic, personal care and household products. It relates to neutralized salts of amines and acids, not to quaternized products of which the anion is exchanged. More specifically, the products are salts of a dicarboxylate and amines which may be partially quaternized. Quaternary amidoamines with unique properties as claimed herein are not disclosed or suggested.

With present-day more stringent detergency requirements it was found that alternative, more efficient detergents are needed, particularly for products that can be used as a detergent in a-polar media.

SUMMARY OF THE INVENTION

The present invention relates to new quaternary fatty amidoamine detergents, the process to make them, and their use.

In an embodiment, the invention relates to the reaction product obtainable by reacting a multifunctional acid with an amino amine, followed by quaternization and subsequent reaction with a fatty acid.

In another embodiment the invention relates to the process wherein a multifunctional acid is reacted with an amino amine, typically an amino alkylene amine, followed by quaternization with a quaternizing agent and subsequent replacement of the anion of said quaternizing agent with a fatty acid anion of choice.

In yet another embodiment the invention relates to the use, as a surface-active agent, of said quaternary fatty amidoamine detergents.

In an embodiment the quaternary amidoamine reaction product is of the formula I):

$$\text{MFA-((NX-alkylene-)}_n\text{N}^+\text{(alkyl)}_2\text{Y}^-)_x \qquad \text{I)}$$

Wherein MFA is the residue of a multifunctional acid with the multifunctionality being defined by x, which is the average number of acid, preferably fatty acid, residues of the multifunctional acid per molecule. In an embodiment x is, on average, 1.3-6.0, n is 1-6, each alkylene is, independently, methylene, ethylene, propylene, and/or (iso)butylene, each X, independently, being H or alkyl, each alkyl, independently, is methyl, ethyl, propyl, or butyl, and Y⁻ is a fatty organic acid anion, it can be carboxylic or an anion of an organic acid with P or S atoms in the acid moiety.

DETAILED DESCRIPTION OF THE INVENTION

The present invention relates to specific quaternary fatty amidoamine detergents that are obtainable by reacting a multifunctional fatty acid with an amino amine, followed by quaternization, suitably with dialkyl carbonate, and subsequent reaction with a fatty carboxylic acid.

Suitably the multifunctional fatty acid is a multifunctional fatty carboxylic acid. In an embodiment the multifunctional acid is an acid with on average 1.1, 1.25, 1.4, 1.5, 1.6, 1.7, 1.75, 1.8, 1.85, or 1.9 acid groups up to 2.1, 2.2, 2.3, 2.4, 2.5, 2.75, 3, 3.5, 4, 5, or 6 acid groups. The acid groups may all be the same or different. In an embodiment the multifunctional acid comprise 8, 9, 10, 11, 12 carbon atoms, up to 14, 15, 16, 18, 20, 22, 24, or 26 carbon atoms per acid function in view of the availability of such multifunctional acids and the fact that these acids provide end-products with the desired solubility in a-polar media. In an embodiment the multifunctional acid is a succinic anhydride of poly-isobutylene (PIBSA). In an embodiment the multifunctional acid is not PIBSA.

The MFA moiety of formula I) is usually a residue of a mixture of oligomerized (mostly dimerized and/or trimerized) unsaturated fatty acids, which are typically formed by means of a Diels Alder reaction. In an embodiment, the oligomerized unsaturated fatty acids, contain 80, 85, 90, 92.5 or more of the dimeric acid. The molecular weight of the MFA is suitably from 300, 350, 400, 450, or 500 up to 600, 800, 1000, 1500, 2500, 5000, 7500 or 10000 D, while still being liquid because of the branched structure and the many isomers present. In an embodiment the MFA is a dimer fatty acid (DFA) as discussed in Kirk-Othmer Encyclopedia of Chemical Technology, 3$^{rd}$ edition, Vol 7, pp 768-782, "Dimer Acids". In an embodiment the dimer fatty acid of the invention is dimerized oleic acid, dimerized tall oil fatty acid, dimerized linoleic acid, or mixtures of one or more of these unsaturated acids. It was noted that unsaturation in the MFA moiety can lead to undesired side-reactions in later processing and handling steps. Therefore, in an embodiment, the MFA moiety is chosen such that it comprises as little as possible unsaturated groups. This can be achieved by starting with a grade of dimerized and/or trimerized acids that is low in unsaturation. However, it can also be achieved by a hydrogenation of all or part of the unsaturated bonds of the MFA moiety at any stage of the process, so before reaction with amidoamine, after reaction with amidoamine but before quaternization, after quaternization, or in the finished end product. Optionally both measures are taken to ensure a low level of unsaturation. In an embodiment, the unsaturation in the finished product is 10, 8, 6, 4, 3, 2, 1, or less double bonds per molecule.

These oligomerized unsaturated fatty acid dimers are widely available and, when reacted as described herein, resulted in products with the proper solubility in an a-polar medium.

The amino amine with which the multifunctional acid is reacted is suitably an amino alkylene amine. In an embodiment it is a tertiary amino alkylene amine of which the amine function has one or two N—H bonds. The alkylene moiety can be linear or branched and typically has from 1 to 8 carbon atoms. In one embodiment, the alkylene is methylene, ethylene, propylene or (iso)butylene. For economic reasons it is suitably ethylene or propylene.

The tertiary amino group comprises one or more methyl, ethyl, propyl, and/or butyl substituents on the nitrogen atom. In an embodiment a tertiary amino group with one or more methyl groups is used since it facilitates the reaction of the tertiary amino group with a quaternizing agent in the subsequent quaternization step.

In an embodiment the amino amine is of the formula II).

(alkyl)$_2$N-(alkylene-NX)$_n$H     II)

with each alkyl independently being methyl, ethyl, propyl, or butyl, alkylene being methylene, ethylene, propylene or (iso)butylene, and each X, independently, being H or C1-4alkyl and n is 1, 2, 3, 4, 5, or 6, suitably 1 or 2.

In an embodiment X=H. In an embodiment each alkylene, independently, is ethylene or propylene. In an embodiment at least one alkyl is methyl. Suitable amino amines include dimethyl amino propyl amine of formula (CH$_3$)$_2$N—C$_3$H$_6$—NH$_2$ and dimethyl amino ethyl amino ethyl amine ((CH$_3$)$_2$N—C$_2$H$_4$—NH—C$_2$H$_4$—NH$_2$).

The ratio wherein multifunctional fatty acid and amino amine are reacted can range widely, depending on x, the multifunctionality of the acid. Suitably, the ratio of number of reactive acid groups of the multifunctional fatty acid:to the number of amine groups NHX equals 2:1 to 1:2, with 1:1 being an equivalent amount. For dimeric fatty acid with (on average) two carboxylic acid groups and an amino amine with one NXH group, the molar ratio of dimer fatty acid: amino amine would hence be from 1:1 to 1:4. If the ratio of reactive groups is too far from equivalent, the product will contain a large amount of raw material which has not reacted, or multifunctional fatty acid or amino amine of which not all acid or NH groups have reacted, which is undesired and requires extensive purification of the product and may adversely affect the solubility in a-polar media. Therefore in an embodiment a ratio of reactive acid:NXH groups of from 1:1 to 1:1.1, 1:1.2, or 1:1.25 is used. It is noted that when n>1 and some of X=H, then some additional acid may be used to react with such secondary amine groups. Excess amino amine can be flashed or purged from the product. In an embodiment excess amino amine is purged at elevated temperatures and recycled to a next batch. Catalysts can be used in the process to influence speed and selectivity. Suitably a catalyst does not comprise chlorine or sulfur atoms since these are typically undesired. In an embodiment no additional catalyst is used in order to avoid purification steps at a later stage. Suitably the reaction takes place at temperatures of from 160 to 220° C. and a pressure which is atmospheric or up to 4 bara (0.4 MPa), preferably using an inert gas such as nitrogen in the gas phase, until at least 85, 90, or 95% completion, typically for 30 minutes to 16 hours. In an embodiment the reaction conditions are chosen such that at least 90% of the acid groups of the multifunctional acid have reacted. In an embodiment the reaction conditions are chosen such that at least 90% of the NHX groups of the amino amine have reacted. In an embodiment the reaction conditions are chosen such both 90% of the acid groups of the multifunctional acid and at least 90% of the NHX groups of the amino amine have reacted.

The amidoamine resulting from the reaction is then quaternized. The quaternized products of the invention must have a specific organic anion, herein also denoted as fatty organic anion, in order to achieve sufficient solubility in a-polar media while still having sufficient charge to act as a detergent. Suitable fatty organic anions are the anions of C1-26 linear or branched, saturated or unsaturated, (partially) aliphatic, (partially) aromatic carboxylic acids, including such organic acids with P or S atoms in the acid moiety, such as those resulting in sulfate, sulfonate, phosphate, phosphonate, or phosphinate anions. In an embodiment the detergent is not based on acids with P or S atoms since such they can be undesired from an environmental perspective. The acids may comprise more than one acid function. If the acid contains more than one acid function, then the acid functions may be the same or different. In an embodiment the organic anions comprise from 1, 2, 4, 6, 8, 9, 10, 11, 12 carbon atoms, up to 14, 15, 16, 18, 20, 22, 24, or 26 carbon atoms per acid function. In an embodiment the acids are salicylic, gallic, toluic acids, dimer fatty acid as mentioned above, or mixtures thereof. Unsaturation of the organic acid leads to some side reaction of the final product at higher temperatures, which can lead to formation of oligomeric, polymeric and/or cross-linked products that precipitate, which is undesired. In an embodiment the anions are therefore anions of saturated C1-C26 or C8-C26 organic acids, their dimers, or mixtures thereof. It was found that such products can be used at higher temperatures (>100 or 200 or 300° C.) while still showing sufficient detergency. In an embodiment of the invention the fatty organic anion comprise 8, 9, 10, 11, 12 or more carbon atoms per acid equivalent because such anions were found to provide the required solubility in a-polar media and the best detergent properties.

A direct quaternization of the amido amine of the invention with such acids was found not to be feasible. However, it was found that an indirect route is economically feasible. In the indirect route, the amido amine is reacted with a conventional quaternizing agent, including products like dialkyl carbonates and dialkyl sulfates. Because of their health and safety characteristics, the use of dialkyl sulfates is less desired. Therefore, in one embodiment, the quaternizing reagent is not dimethyl sulfate. Also because it is often preferred that the final product is chlorine-free, sulfur-free, and phosphate-free the use of a dialkyl carbonate as the initial quaternizing reagent is typically preferred. Also it was found that in a subsequent counter ion-exchange step, an alkyl carbonate anion is easily and completely removed. Therefore, in an embodiment, a dialkyl carbonate is used as a quaternizing agent of the amidoamine. Indicative of the reaction of the tertiary amine function of the amidoamine with a quaternizing agent like dimethyl carbonate is the following pathway:

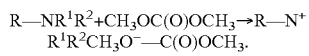
R—NR$^1$R$^2$+CH$_3$OC(O)OCH$_3$→R—N$^+$R$^1$R$^2$CH$_3$O$^-$—C(O)OCH$_3$.

However, also other quaternization reactions followed by introduction of the suitable acid counter ion, as mentioned above, are foreseen.

Because of ease of reaction and because this route generates little by-products and contaminants, in one embodiment the quaternary amidoamine detergent of the invention is obtained by reacting the above described amido amine with a dialkyl carbonate and a subsequent reaction of the resulting quaternary ammonium compound alkyl carbonate, with an organic acid, a dimer thereof, esters thereof, or mixtures thereof. In an embodiment the organic acid comprises one or more from C8, C9, or C10 up to C14, C16, or C18 carboxylic acids. Indicative of the ion exchange reaction of the quaternized material with an acid like carboxylic acid, is the following pathway:

R—N$^+$R$^1$R$^2$CH$_3$O$^-$—C(O)OCH$_3$+R$^3$—COOH→R—N$^+$R$^1$R$^2$CH$_3$O$^-$—C(O)R$^3$+CO$_2$+methanol.

Removal of CO$_2$, if so desired by lowering the pressure in the reactor, will drive the reaction to completion.

Irrespective of the embodiment used, the fatty acid anion is of an organic acid which is suitably derived from a natural source, such as coconut, laurel, palm, palm kernel, cottonseed, olive, hemp, soybean, tall oil, or tallow fats or oils. In embodiments where a saturated acid is desired, coconut-based products are preferred for their low unsaturation. For some uses a product may be required, e.g. for quality reasons, which does not tolerate a product with an ill-defined composition, such as those resulting when acids mixtures from natural sources are used. In that case, for instance, pure compounds can be used, such as a purified mixture of acids natural sources, or products like pure lauric acid.

In an embodiment the fatty acid anion is the anion of a fatty acid that is soluble in water (at 20° C. and atmospheric pressure) for less than 10, 5, 3.3, 1.1, 1, or 0.75 g per 100 g of water.

In an embodiment, the quaternized products of the invention are essentially free from products where part of amine groups of the molecule are neutralized with an acid under formation of a salt. Essentially free from meaning that less than 20%, 10%, 5%, 2%, 1% or 0.75% or tertiary amine groups, based on all tertiary amine groups in the product, are neutralized with an acid. Since salts adversely influence the solubility of the quaternized products in an a-polar medium.

In an embodiment the dialkyl carbonate used in this process is dimethyl carbonate, diethyl carbonate, or a mixture thereof. Because of its availability dimethyl carbonate (DMC) can be preferred. If traces of methanol in the end-product are troublesome it can be advantageous to use diethyl carbonate (DEC) as the quaternizing agent. In an embodiment the amount of dialkyl carbonate used in the quaternization step is equivalent or more than equivalent in order to reduce side products in the final quaternary fatty amidoamine detergent. In an embodiment wherein a dimeric fatty acid is used as the multifunctional acid, the molar ratio of dialkyl carbonate to dimer fatty acid amidoamine is suitably from 2, 2.5, 3, 3.5, or 4 to 1. More generally, the ratio of equivalents of dialkyl carbonate to tertiary amine groups of the amidoamine is from 1, 1.25, 1.5, 1.75, or 2 to 1. In an embodiment the equivalent ratio is from 1.5-2 to 1. In the process suitably an alcohol with 1 to 14 carbon atoms is used as a solvent. In an embodiment the solvent is methanol or ethanol because it can be easily flashed off. In an embodiment the solvent is methanol when DMC is the quaternizing agent and ethanol when DEC is used, since in that case the solvent formed in the reaction with the fatty acid is the same as the solvent used in the quaternization step, facilitating recovery and recycle of the solvents. For the reaction with DMC temperatures are of from 80 to 140° C., the pressure is suitably 0.1-0.6 MPa, for a period of from 4 to 24 hours. Suitably a temperature of about 110° C., at a pressure of about 0.35 MPa, for about 8 hours is used. Residual amounts of DMC and solvent are removed with vacuum and/or nitrogen stripping. Any recovered dialkyl carbonate and alcohol is suitably recycled for re-use in the quaternization step, optionally after purification.

In the subsequent reaction with acid, wherein the anion of the quaternizing agent is replaced with the anion of the reacting fatty acid, the reaction can be forced to completion by removal of CO$_2$ and/or the solvent used and formed, e.g. methanol if DMC and ethanol if DEC is used as the quaternizing agent. As before, the recovered solvent can be recycled to the quaternization step. Since typically (m)ethanol is being formed in the anion replacement step, typically not all (m)ethanol can be recycled. Therefore there typically is also a purge for the solvent that is retrieved from the quaternization or ion replacement step.

The fatty acid used to form the new counter ion has to be carefully selected in order to get the proper solubility in a-polar media while also having good detergency power. Typically the acids are carboxylic acids, anhydrides, acid chlorides, or carboxylic acid esters. Such acids form the corresponding anions. However, the anion can also be an organic sulfate, sulfonate, phosphate, phosphonate, or phosphinate ion, by using the corresponding acids thereof. Typically mono-functional acids are used in the ion exchange reaction. However, if so desired, also di, tri, tetra, or poly-acids can be used. Mono fatty carboxylic acids are preferred in view of their wide abundance and since they are easily processed since they react fast and do not lead to viscosity-related issues in the factory. After extensive testing it was found that the use of anions with a hydrocarbon group with on average from 8, 10, or 12 up to 26, 20, 18, 16, or 14 carbon atoms per anion resulted in the best solubility and detergency. The anion may contain (partially) cyclic functionality, as in (linear) dodecyl benzene sulfonates. However, fully saturated acids may be preferred for environmental reasons. The hydrocarbon part of the acids can be linear or branched, whereby linear products may be preferred for their rheological profile. Suitably the majority (more than 50% by weight) of the hydrocarbon groups of the acid have from 11 or 12 up to 14 or 15 carbon atoms per anion since they were found to give the best surface-active properties. Suitably, a naturally occurring fat or oil is used as the source of the anions. Hence, the acid is suitably derived from products like tallow, palm, and coconut fat/oil since they require little purification. In an embodiment coconut-based fatty acids are used that have been fractionated so they contain predominantly (>90% by weight) of C12 and C14 fatty acid. Such a fractionated fatty acid mixture is commercially available as "mid-cut coco". Suitable the mid-cut coco is hardened before use to make a quaternary fatty amidoamine of the invention. Any hardening can take place before or after the acid is used to replace the original anion. If done after the ion exchange step, this can have the benefit that all unsaturated bonds in the whole molecule are hydrogenated, which can have positive effects, like increased heat stability, easier handling and a broader potential use of the product.

Quaternary fatty amidoamine made with said saturated, non-substituted fatty acid-derived anions were found to have the desired solubility in hydrocarbons, and C8 and higher liquid alcohols. Since the fatty acids are preferably from a natural source that is abundant, the fatty acids are suitably derived from coconut oil, laurel oil, and/or palm kernel oil. In an embodiment they do not comprise any unsaturated fatty acid, for instance by using hardened oil or fat. In an embodiment more than 50, 60, 70, 75, or 80% by weight of the fatty acid is lauric acid, myristic acid, or a combination thereof, since quaternary dimer fatty amido alkylene amine compounds with those counter-ions gave best performance in detergency and stabilization of solids while being soluble in all oils and alcohols of interest and leading to products with a low melting point. In an embodiment the products are liquid at temperatures of 20° C. and higher. In an embodiment the fatty acid anion is substantially free of fatty acid ions with 18, or more carbon atoms since quaternary dimer fatty amido alkylene amine compounds with such anions were found to have reduced solubility leading to undesired precipitation, particularly when used in oils to stabilize solids dispersed therein. In an embodiment the solubility in 2-ethyl hexanol is more than 50, 60, 70, or 75% by weight. Such formulations were found to have a high flash point and easy handling.

In an embodiment the quaternized amido amine of the invention comprises products of the formula (III) that are based on dimerized fatty acids. Depending on the MFA used, there may be products with more X groups (e.g. three if trimerized fatty acids are in the starting MFA.

(III)

wherein
A, B, C and D represent, independently to each other, an alkyl or an alkenyl group with a number of carbon atoms resulting in a molar mass of A+B+C+D ranging from 84 to 10,000 g/mol, and whereby A is optionally hydrogen;
Each X, independently to each other, represents the monovalent radical of formula (IV):

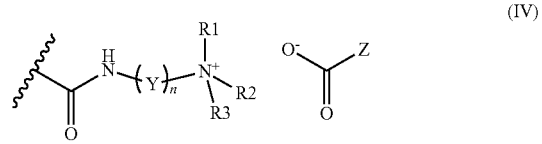

(IV)

wherein
Each R1, R2, R3, independently to each other, is a $C_1$-$C_{20}$ linear or branched, saturated or unsaturated, cyclic or acyclic, hydrocarbyl group;
Each Y, independently to each other, is a $C_1$-$C_{20}$ linear or branched, saturated or unsaturated, hydrocarbyl group optionally substituted by a functional group comprising oxygen and/or a nitrogen atom(s);

Each n, independently to each other, is an integer ranging, on average, from 1 to 20;
Each ZCOO⁻, independently to each other, represents the anion of a fatty acid as defined above, and Z is suitably a $C_1$-$C_{16}$, linear or branched, saturated or unsaturated, cyclic or acyclic, hydrocarbyl group optionally substituted by a functional group comprising an oxygen and/or a nitrogen atom.

In an embodiment both X groups in formula III are identical.

In the formula (III) above, A, B, C and D represents, independently to each other, an alkyl or an alkenyl group with a number of carbon atoms resulting in a molar mass of A+B+C+D ranging from 84 to 10000 g/mol. The molar mass of A+B+C+D corresponds to the sum of the molar mass of A, B, C and D groups. Preferably, the molar mass of A+B+C+D ranges from 84 to 2000 g/mol, more preferably from 84 to 1000 g/mol, even more preferably from 200 to 750 g/mol.

According to an embodiment, A, B, C and D represents, independently to each other, an alkyl or an alkenyl group comprising from 2 to 16 carbon atoms, preferably from 4 to 12 carbon atoms. According to an embodiment, at least one among A, B, C and D groups represents an alkenyl group preferably comprising from 2 to 16 carbon atoms, more preferably from 4 to 12 carbon atoms. According to an embodiment, A or B is an alkenyl group preferably comprising from 2 to 16 carbon atoms, more preferably from 4 to 12 carbon atoms, even more preferably from 6 to 10 carbon atoms. In an embodiment A is hydrogen. In an embodiment A is not hydrogen.

According to an embodiment, A and B are different groups.

According to an embodiment, C and D are different groups.

According to an embodiment, each A, B, C and D group comprises less than 4, preferably less than 3, more preferably less than 2, carbon-carbon double bonds. According to an embodiment, all A, B, C and D groups (considered together) comprise less than 4, preferably less than 3, more preferably less than 2, carbon-carbon double bonds.

In the formula (IV) above, R1, R2, R3, identical or different, represent a $C_1$-$C_{20}$ linear or branched, saturated or unsaturated, cyclic or acyclic, hydrocarbyl group. According to an embodiment, the hydrocarbyl group is acyclic and constituted by carbon atoms and hydrogen atoms.

According to an embodiment, R1, R2 and R3, identical or different, represent a $C_1$-$C_{20}$ linear or branched alkyl or alkenyl group, preferably a $C_1$-$C_{20}$ linear or branched alkyl group, more preferably a $C_1$-$C_{20}$ linear alkyl group. According to an embodiment, R1, R2 and R3, identical or different, represent a $C_1$-$C_{12}$ linear or branched alkyl or alkenyl group, preferably a $C_1$-$C_{12}$ linear or branched alkyl group, more preferably a $C_1$-$C_{12}$ linear alkyl group. According to an embodiment, R1, R2 and R3, identical or different, represent a $C_1$-$C_6$ linear or branched alkyl or alkenyl group, preferably a $C_1$-$C_6$ linear or branched alkyl group, more preferably a $C_1$-$C_6$ linear alkyl group. Preferably, R1, R2 and R3 are identical and represent a methyl, ethyl or propyl group, preferably a methyl group.

In the formula (IV) above, Y represents a $C_1$-$C_{20}$ linear or branched, saturated or unsaturated, hydrocarbyl group optionally substituted by a functional group comprising oxygen and/or a nitrogen atom(s). According to an embodiment, Y represents a $C_1$-$C_{12}$ linear or branched, saturated or unsaturated, acyclic hydrocarbyl group optionally substituted by a functional group comprising oxygen and/or a nitrogen atom(s). According to an embodiment, Y represents a $C_1$-$C_{20}$ linear or branched, saturated or unsaturated, aliphatic hydrocarbyl group constituted by carbon atoms and hydrogen atoms. According to an embodiment, Y represents a $C_1$-$C_{20}$ linear or branched alkyl or alkenyl group, preferably a $C_1$-$C_{20}$ linear or branched alkyl group, more preferably a $C_1$-$C_{20}$ linear alkyl group. According to an embodiment, Y represents a $C_1$-$C_{12}$ linear or branched alkyl or alkenyl group, preferably a $C_1$-$C_{12}$ linear or branched alkyl group, more preferably a $C_1$-$C_{12}$ linear alkyl group. According to an embodiment, Y represents a $C_1$-$C_6$ linear or branched alkyl or alkenyl group, preferably a $C_1$-$C_6$ linear or branched alkyl group, more preferably a $C_1$-$C_6$ linear alkyl group, even more preferably a $C_1$-$C_4$ linear alkyl group.

In the formula (IV) above, n represents an integer ranging from 1 to 20, preferably from 1 to 16, more preferably from 1 to 12, even more preferably from 1 to 8, ideally from 1 to 4. In an embodiment Z represents a $C_1$-$C_{16}$, linear or branched, saturated or unsaturated, cyclic or acyclic, aliphatic or aromatic hydrocarbyl group optionally substituted by a functional group comprising an oxygen and/or a nitrogen atom. According to an embodiment of the invention, Z is selected from alkyl, alkenyl or aryl groups, optionally substituted by a functional group comprising oxygen and/or a nitrogen atom(s), having a molar mass strictly less than 237 g/mol, preferably less than 210 g/mol. In an embodiment, Z represents a group selected from:
  aryl groups optionally substituted by a functional group comprising oxygen and/or nitrogen atom(s),
  linear or branched alkenyl groups comprising from 2 to 15 carbon atoms, and
  linear or branched alkyl groups comprising from 1 to 15 carbon atoms.
In an embodiment, Z represents a group selected from:
  aryl groups substituted by a functional group comprising oxygen and/or nitrogen atom(s),
  linear alkenyl groups comprising from 2 to 15 carbon atoms, and
  linear alkyl groups comprising from 1 to 15 carbon atoms.
In an embodiment, Z represents a group selected from:
  a phenyl group substituted by a hydroxyl function preferably in ortho position,
  linear or branched, preferably linear, alkenyl groups comprising from 2 to 15 carbon atoms, and
  linear or branched, preferably linear, alkyl groups comprising from 1 to 15 carbon atoms.
In an embodiment, Z represents a group selected from:
  a phenyl group optionally substituted by a functional group comprising oxygen and/or nitrogen atom(s), and
  linear or branched alkyl groups comprising from 1 to 15 carbon atoms.
In an embodiment, Z represents a group selected from:
  a phenyl group substituted, preferably in ortho position, by a functional group comprising oxygen and/or nitrogen atom(s), preferably by a hydroxyl group, and
  linear alkyl groups comprising from 1 to 15 carbon atoms.
In an embodiment, Z represents a $C_1$-$C_{16}$ linear or branched, saturated or unsaturated, aliphatic hydrocarbyl group optionally substituted by a functional group comprising an oxygen and/or a nitrogen atom.
In an embodiment, Z represents a group selected from:
  linear or branched alkenyl groups comprising from 2 to 16 carbon atoms, preferably from 5 to 16 carbon atoms, and
  linear or branched alkyl groups comprising from 1 to 16 carbon atoms, preferably from 5 to 16 carbon atoms.

In an embodiment, Z represents a group selected from linear or branched alkyl groups comprising from 1 to 18 carbon atoms, preferably from 5 to 16 carbon atoms.

In an embodiment, the number of quaternized amine functions is comprised between 65%, 70%, 75%, 80%, 90%, or 95% and 100%, based on the total number of quaternizable amine functions.

In an embodiment the invention relates to compositions comprising molecules with the structure

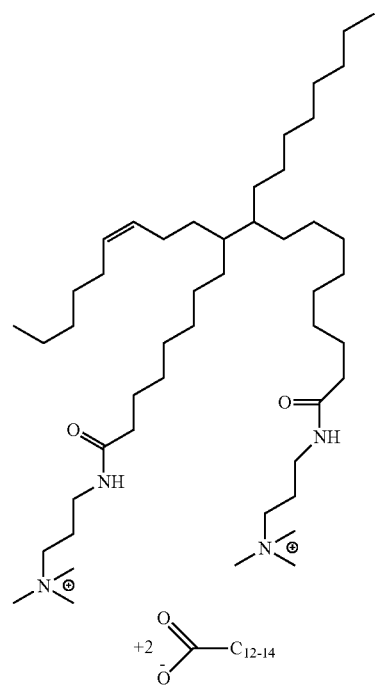

the process to make them, and their use.

The fatty acids are easily reacted with quaternary dimer fatty amido alkylene amine with (m)ethocarbonate anions under liberation of $CO_2$ and methanol. Typically 1 or 1.1 up to 2, 1.75, 1.5, or 1.25 moles of fatty acid are used per mole of anion on the quaternary dimer fatty amido alkylene amine. The reaction is suitably carried out at 60-120° C., at atmospheric pressure in 0.5-2 h. Residual amounts of $CO_2$ and methanol are removed under vacuum or by nitrogen stripping, suitably at temperatures of from 60 to 140° C. ay a pressure which is lowered from atmospheric to <0.0005 MPa.

In another embodiment the invention relates to the process to make the products of claim 1 comprising the steps of
  reacting a multifunctional fatty acid with an amino amine to form an amidoamine
  quaternization of the amidoamine with a quaternizing agent to form a quaternary ammonium compound with certain anions, and
  replacing the anion of the quaternary compound with another acid anion.

Details of the process are presented above. In an embodiment a solvent in which the quaternary fatty amidoamine detergent is soluble is used in any part of the process, to lower the viscosity and increase reaction rates. This solvent can be removed from, or added to, intermediates and be removed or left in the end product as a diluent. Suitably solvent is removed by distillation.

In an embodiment the products are used in concentrated suspensions of solids in oils, or other a-polar media, as when making agrochemical dispersions, or for use in the oil production industry, e.g. in oil well drilling operations, the use in a demulsification step, the use to prevent corrosion, and/or the use to avoid formation of gas hydrates. When making agrochemical dispersions, the agrochemical compound being dispersed is suitably a pesticide, a fertilizer, or both.

In yet another embodiment the invention relates to the use, as a detergent or stabilizer of solids, of the reaction products of claim 1 in a-polar media.

When a ratio or amount is given, it is by weight, unless mentioned differently.

Throughout this document, unless indicated differently, the weight percentages of the compositions are based on the total weight of the composition, whereby the total weight of the composition is 100 wt %. The term water-soluble is used for materials that dissolve in an amount of at least 1 g per liter of demineralized water at 25° C. Where used, the term "consisting" also embraces "consisting substantially", but may optionally be limited to its strict meaning of "consisting entirely". An a-polar (nonpolar) medium is herein defined as a material having a dielectric coefficient of less than 7 at 20° C. Typically it is a liquid at the temperature of use. Suitably it is a medium with a dielectric coefficient at 20° C. of less than 6.5, 6, 5.5, 5, 4.5, 4, 3.5, or 3. The dielectric constant is measured in accordance with ASTM D150. The term "substantially free" is used for a moiety that is present in an amount of less than 2% by weight. Similarly, the term "essentially" is used to denote a composition that consists for more than 95% by weight of the indicated components.

Throughout the description and claims of this specification, the words "comprise" and "contain" and variations of the words, for example "comprising" and "comprises", mean "including but not limited to", and do not exclude other moieties, additives, components, integers or steps. Moreover the singular encompasses the plural unless the context otherwise requires: in particular, where the indefinite article is used, the specification is to be understood as contemplating plurality as well as singularity, unless the context requires otherwise.

Where upper and lower limits are quoted for a property, for example for the concentration of a component, then a range of values defined by a combination of any of the limits is disclosed and meant.

It will also be appreciated that features from different aspects and embodiments of the invention may be combined with features from any other aspect and embodiment of the invention.

Although the invention is illustrated and described herein with reference to specific embodiments, the invention is not intended to be limited to the details shown. Rather, various modifications may be made in the details within the scope and range of equivalents of the claims. More specifically, where reaction conditions are presented, they have typically not been optimized, whereby the optimized conditions are within the scope of the claims.

The present invention will now be illustrated by the following non-limiting examples.

EXAMPLES

Materials:
Dimer fatty acid: Pripol® 1013 ex Croda GmbH,
Aminoamine: Dimethylpropylamine: 3-(dimethylamino)-1-propylamine (98%) 39380 ex Sigma Aldrich,
Dimethylcarbonate: Dimethyl carbonate Reagent plus (99%) D152927 ex Sigma Aldrich,
2-ethyl-1-hexanol: 2-Ethyl-1-hexanol 99% 04050 ex Sigma Aldrich,
Mid-cut coco fatty acid: A mixture of lauric acid, myristic acid and palmitic acid ex Pacific Oleochemicals Sdn. Bhd as well as Kortacid® 1299/1499/1698 ex Sigma Aldrich. (about 75% C12 and about 25% C14 and less than 5% w/w C16).

Preparation Example 1

1 mole (573 g.) of dimer fatty acid is reacted with 2.4 moles (245 g.) of dimethyl amino propyl amine (DMAPA). 1.4 g. of 50% $H_3PO_2$ is added as catalyst. The temperature is increased in 5 h. to 190° C. and maintained for 3 h. at atmospheric conditions. Excess DMAPA is removed at 190° C. and 20 mbara.

1 mole (730 g) of the amidoamine from the previous step is reacted with 4 moles of dimethyl carbonate (360 g.) in 360 g. of methanol. The reaction mixture is heated for 8 h. at 110° C. and 3.5 bara. The excess dimethyl carbonate and methanol are removed at 90° C. and 5 mbara. To prevent gelation some 225 g. (20%) of 2-ethyl-1-hexanol is added.

To 1 mole of the dimer amido quat (910 g) in 225 g of 2-ethyl-1-hexanol solvent, 2.2 moles (458 g) of mid-cut coco fatty acid is added at 90° C. and atmospheric pressure. Residual $CO_2$ and methanol are removed at 90° C. and 5 mbara for 1 h. The obtained product can be diluted with 2-ethyl-1-hexanol to obtain a 50% active product and has the formula

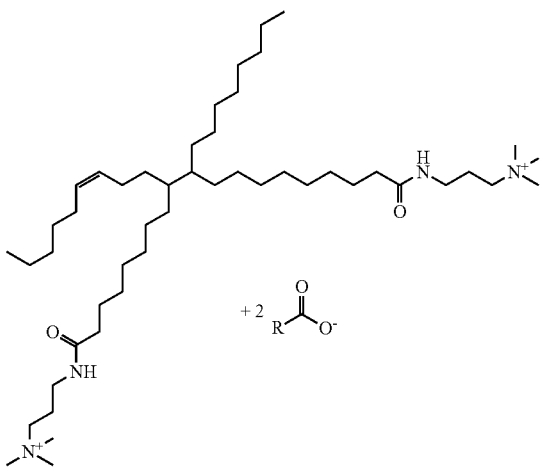

with R is a mixture of essentially linear C11 and C13 alkyl.

Use Example 2

The product of preparation example 1 was found to easily dissolve in an a-polar medium, and was found to provide excellent detergent power to the dissolution and to perfectly stabilize a dispersion of solids in said dissolution, over a wide range of temperatures.

What is claimed is:
1. Quaternary amidoamine obtained by
forming amidoamines by reacting one or more multifunctional fatty acids comprising from 8 to 26 carbon atoms per acid function of said multifunctional fatty acids with on average from 1.1 to 6.0 acid groups, with one or more amino amines of formula II)

(alkyl)$_2$N-(alkylene-NX)$_n$H    II)

wherein each alkyl independently is selected from methyl, ethyl, propyl, and butyl, wherein each alkylene independently is selected from methylene, ethylene, propylene or (iso)butylene, and each X, independently, is H or C1-4 alkyl and n is 1, 2, 3, 4, 5, or 6, followed by quaternizing amine functions of the amidoamine with a quaternizing agent that is halogen-free, sulfur-free, and phosphate-free to form a quaternary ammonium compound, and subsequently reacting the quaternary ammonium compound with one or more fatty acids comprising 8 to 26 carbon atoms to exchange an anion of the quaternizing agent by an anion of said fatty acid.

2. Quaternary amidoamine of claim 1 wherein the one or more multifunctional acids is a dimerized fatty acid derived from oleic acid, tall oil fatty acid, linoleic acid, or mixtures thereof.

3. Quaternary amidoamine of claim 1, wherein X is H, each alkylene, independently, is ethylene or propylene, and at least one alkyl is methyl.

4. Quaternary amidoamine of claim 1, wherein the one or more fatty acids are selected from C8-26 linear or branched, saturated or unsaturated, fatty acids, dimer fatty acid.

5. Quaternary amidoamine of claim 4 wherein the one or more fatty acids are carboxylic acids.

6. Quaternary amidoamine of claim 4, wherein the one or more fatty acids are non-substituted.

7. Quaternary amidoamine of claim 4, wherein the one or more fatty acids comprise, on average, from 12 to 18 carbon atoms.

8. Quaternary amidoamine of claim 1, wherein the anion of the one or more fatty acid is fully saturated.

9. Quaternary amidoamine of claim 8, which is fully saturated.

10. Process to make the quaternary amidoamine of claim 1, comprising the steps of:

reacting a multifunctional fatty acid with on average from 1.1 to 6.0 acid comprising from 8 to 26 carbon atoms per acid function of said multifunctional fatty acid groups with an amino amine (alkyl)$_2$N-(alkylene-NX)$_n$H, wherein each alkyl independently is selected from methyl, ethyl, propyl, and butyl, wherein each alkylene independently is selected from methylene, ethylene, propylene or (iso)butylene, and each X, independently, is H or C1-4 alkyl and n is 1, 2, 3, 4, 5, or 6, to form an amidoamine, quaternizing the amidoamine with a quaternizing agent to form a quaternary ammonium compound with an anion of said quaternizing agent, and replacing said anion with the anion of a fatty acid comprising 8 to 26 carbon atoms by reaction of the quaternary ammonium compound with one or more fatty acids.

11. Quaternary amidoamine of claim 1 wherein the step of quaternizing is free of dimethyl sulfate.

12. Quaternary amidoamine of claim 1 wherein the quaternizing agent is dimethylcarbonate.

13. Quaternary amidoamine of claim 12 wherein the amino amine is dimethylpropylamine.

14. Quaternary amidoamine of claim 13 wherein the one or more multifunctional acids is dimerized oleic fatty acid.

15. Quaternary amidoamine of claim 14 wherein the one or more fatty acids are a mixture of lauric acid, myristic acid and palmitic acid.

16. The process of claim 10 wherein the quaternizing agent is dimethylcarbonate.

17. The process of claim 10 wherein the step of quaternizing is free of dimethyl sulfate.

18. Quaternary amidoamine obtained by forming amidoamines by reacting a dimerized fatty acid derived from oleic acid, tall oil fatty acid, linoleic acid, or mixtures thereof, with one or more amino amines of formula II)

(alkyl)$_2$N-(alkylene-NX)$_n$H    II)

wherein each alkyl independently is selected from methyl, ethyl, propyl, and butyl, wherein each alkylene independently is selected from methylene, ethylene, propylene or (iso)butylene, and each X, independently, is H or C1-4 alkyl and n is 1, 2, 3, 4, 5, or 6, followed by quaternizing amine functions with a quaternizing agent that is halogen-free, sulfur-free, and phosphate-free to form a quaternary ammonium compound, and subsequently reacting the quaternary ammonium compound with one or more fatty acids comprising 8 to 26 carbon atoms to exchange an anion of the quaternizing agent by an anion of said fatty acid, wherein the step of quaternizing is free of dimethyl sulfate.

19. Quaternary amidoamine of claim 18 wherein:
the dimerized fatty acid is dimerized oleic fatty acid;
the amino amine is dimethylpropylamine;
the quaternizing agent is dimethylcarbonate; and
the one or more fatty acids are a mixture of lauric acid, myristic acid and palmitic acid.

* * * * *